US011109890B2

(12) United States Patent
Druma et al.

(10) Patent No.: US 11,109,890 B2
(45) Date of Patent: Sep. 7, 2021

(54) VERTEBRAL BODY ACCESS CANNULA WITH ENHANCED BENDING STIFFNESS

(71) Applicant: Medtronic Holding Company Sàrl, Tolochenaz (CH)

(72) Inventors: Calin Druma, San Jose, CA (US); Samuel Bolosan, San Jose, CA (US); Hester Chan, Sunnyvale, CA (US)

(73) Assignee: KYPHON SARL, Neuchatel (CH)

( * ) Notice: Subject to any disclaimer, the term of this patent is extended or adjusted under 35 U.S.C. 154(b) by 147 days.

(21) Appl. No.: 15/879,487

(22) Filed: Jan. 25, 2018

(65) Prior Publication Data

US 2019/0223901 A1 Jul. 25, 2019

(51) Int. Cl.

| | |
|---|---|
| ***A61B 17/34*** | (2006.01) |
| ***A61B 17/88*** | (2006.01) |
| ***A61B 17/70*** | (2006.01) |
| ***A61B 17/17*** | (2006.01) |
| ***A61B 17/16*** | (2006.01) |
| *A61B 5/00* | (2006.01) |

(52) U.S. Cl.

CPC ...... *A61B 17/3421* (2013.01); *A61B 17/3472* (2013.01); *A61B 17/7094* (2013.01); *A61B 17/7097* (2013.01); *A61B 17/8855* (2013.01); *A61B 17/8858* (2013.01); *A61B 5/6853* (2013.01); *A61B 17/1642* (2013.01); *A61B 17/1757* (2013.01); *A61B 17/8805* (2013.01); *A61B 17/8811* (2013.01); *A61B 2017/3454* (2013.01)

(58) Field of Classification Search

CPC . A61B 17/88; A61B 17/8855; A61B 17/8811; A61B 17/3421; A61B 17/3472; A61B 17/7094; A61B 17/7097; A61B 17/1642; A61B 17/1757; A61B 17/8805; A61B 2017/3454; A61B 5/6853; A61B 17/8858

USPC ........................................................ 606/92

See application file for complete search history.

(56) References Cited

U.S. PATENT DOCUMENTS

| | | | |
|---|---|---|---|
| 6,132,413 A | 10/2000 | Mathias et al. | |
| 6,425,859 B1 * | 7/2002 | Foley .................... | A61B 17/02 600/204 |
| 8,043,279 B2 | 10/2011 | Hisamatsu et al. | |
| 8,377,036 B2 | 2/2013 | Jonkman | |
| 8,535,211 B2 | 9/2013 | Campbell et al. | |

(Continued)

FOREIGN PATENT DOCUMENTS

| | | |
|---|---|---|
| CN | 2936282 Y | 8/2007 |
| CN | 204600540 U | 9/2015 |

(Continued)

*Primary Examiner* — Marcela I. Shirsat
(74) *Attorney, Agent, or Firm* — Sorell, Lenna & Schmidt, LLP

(57) ABSTRACT

A kyphoplasty cannula includes a shaft extending between opposite first and second end surfaces. The shaft has an inner surface defining a lumen. The shaft has a first opening that extends through the first end surface and a second opening that extends through the second end surface. A scoop extends from the second end surface. The scoop has an arcuate inner surface that is continuous with the inner surface of the shaft an opposite outer surface. The scoop has a rib. Kits and methods of use are disclosed.

18 Claims, 24 Drawing Sheets

(56) References Cited

U.S. PATENT DOCUMENTS

| | | | | |
|---|---|---|---|---|
| 8,709,362 | B2 * | 4/2014 | Leventhal | B01L 3/18 422/547 |
| 2003/0236447 | A1 * | 12/2003 | Ritland | A61B 17/1757 600/210 |
| 2004/0162519 | A1 | 8/2004 | Helkowski et al. | |
| 2006/0004346 | A1 | 1/2006 | Begg | |
| 2007/0282269 | A1 | 12/2007 | Carter et al. | |
| 2013/0013007 | A1 * | 1/2013 | Broome | A61B 17/8811 606/86 R |
| 2014/0235997 | A1 * | 8/2014 | Smith | A61B 6/12 600/424 |
| 2015/0165110 | A1 | 6/2015 | Gopalakrishna et al. | |
| 2017/0087287 | A1 | 3/2017 | Keenan et al. | |
| 2017/0164978 | A1 * | 6/2017 | Dean | A61B 17/3472 |
| 2019/0201066 | A1 * | 7/2019 | Sasaki | A61B 17/8811 |

FOREIGN PATENT DOCUMENTS

| | | | |
|---|---|---|---|
| WO | 2006098894 | A1 | 9/2006 |
| WO | 2007036815 | A2 | 4/2007 |
| WO | 2011159613 | A2 | 12/2011 |
| WO | 201411042 | A1 | 7/2014 |

* cited by examiner

| EQUIVALENT PLASTIC STRAIN (in/in) | | |
|---|---|---|
| CANNULA 68 | CANNULA 22 (SHOWN IN FIG. 1-3) | CANNULA 22 (SHOWN IN FIG. 4-6) |
| 0.0392365 (MAX) | 0.13139 (MAX) | 0.0087888 (MAX) |
| 0.034902 | 0.010219 | 0.0078123 |
| 0.026177 | 0.008759 | 0.0068358 |
| 0.021814 | 0.0072992 | 0.0058592 |
| 0.017451 | 0.0058394 | 0.0048827 |
| 0.013088 | 0.0043795 | 0.0039061 |
| 0.0087255 | 0.0029197 | 0.0029296 |
| 0.0043628 | 0.0014598 | 0.0019531 |
| 0 | 0 | 0 |

*FIG. 18*

VERTEBRAL BODY ACCESS CANNULA WITH ENHANCED BENDING STIFFNESS

TECHNICAL FIELD

The present disclosure generally relates to surgical devices, and more particularly to a scoop cannula with enhanced bending stiffness configured for use in a kyphoplasty procedure. Kits and methods of use are disclosed.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting one or more balloons, such as, for example, compliant balloons inside a fractured vertebral body. The balloon or balloons are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

The balloons may be inserted into the vertebral body using a cannula, for example. Some cannulas include a scoop at the end of the cannula. The balloon engages the scoop to direct inflation of the balloon so that the balloon inflates away from the scoop. However, conventional scoop cannulas tend to plastically deform when the balloon is inflated, which may cause the cannula to break. For example, the cannula may plastically deform when the balloon is inflated such that the scoop breaks off from a shaft of the cannula. This disclosure describes improvements over these prior art technologies.

SUMMARY

In one embodiment, a kyphoplasty cannula comprises a shaft extending between opposite first and second end surfaces. The shaft comprises an inner surface defining a lumen. The shaft comprises a first opening that extends through the first end surface and a second opening that extends through the second end surface. A scoop extends from the second end surface. The scoop comprises an arcuate inner surface that is continuous with the inner surface of the shaft and an opposite outer surface. The scoop including a rib that is configured to increase the stiffness of the scoop and provide additional support to the cannula to reduce the amount of plastic deformation that the cannula undergoes due to the inflation of a balloon against the scoop, as discussed herein. In some embodiments, kits and methods of use are disclosed.

BRIEF DESCRIPTION OF THE DRAWINGS

The present disclosure will become more readily apparent from the specific description accompanied by the following drawings, in which:

FIG. 18 is a table showing equivalent plastic strain of the cannulas shown in FIGS. 1-6 and 17;

Like reference numerals indicate similar parts throughout the figures.

DETAILED DESCRIPTION

Figure 1:
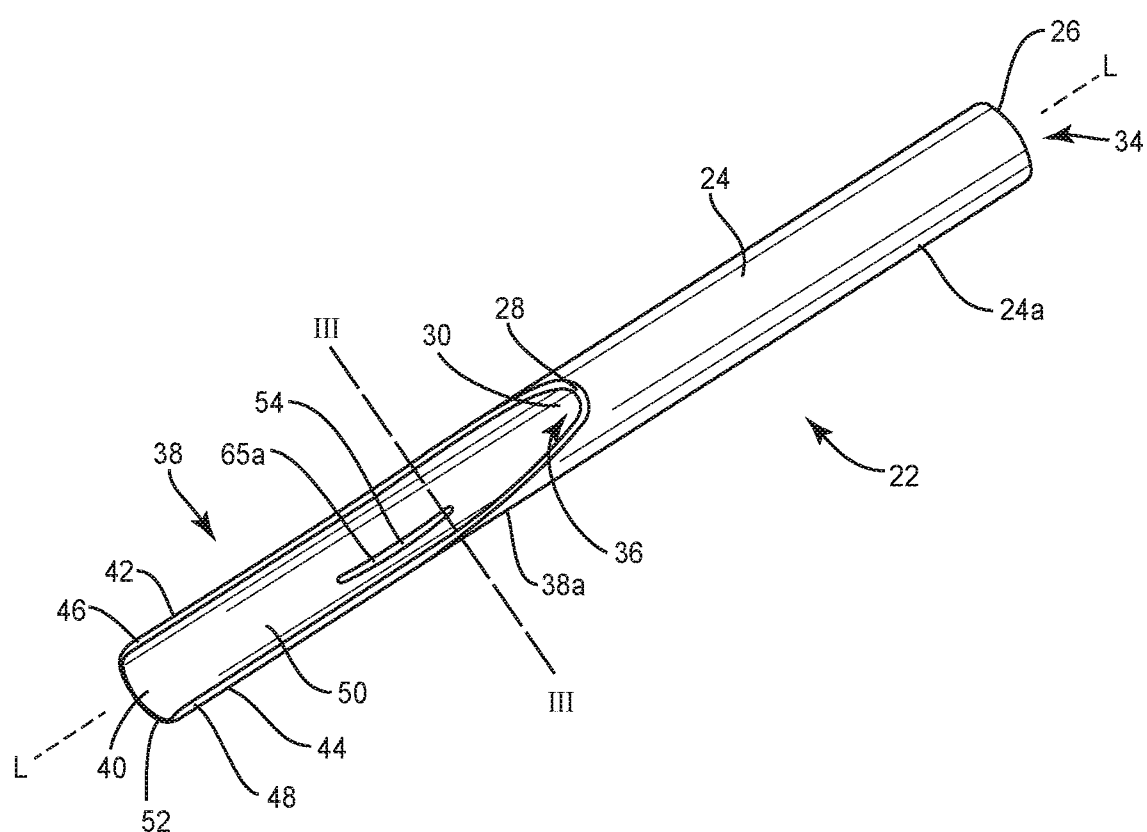
FIG. 1 is a perspective view of one embodiment of a component of a surgical system, in accordance with the present principles of the present disclosure.

The exemplary embodiments of a surgical system, kit and related methods are discussed in terms of medical devices for performing kyphoplasty. In some embodiments, the system includes a cannula. The cannula has a semicircular plateau at the distal tip that protects one region of a vertebral body while leaving another region of the vertebral body exposed. A balloon may be inflated against the semicircular plateau that is supported on the contralateral side by bone and inflate preferentially on the opposite side of the cannula plateau. The cannula includes a rib or wrinkle along the plateau of the cannula. In some embodiments, the cannula can include either one or a plurality of ribs or wrinkles that lay on the cannula's maximum bending stress. The rib(s) or wrinkle(s) increase the stiffness of the construct and provides additional support to the cannula, therefore reducing the amount of plastic deformation that the cannula undergoes due to the balloon inflation versus a cannula that does not include rib(s) or wrinkle(s) on the cannula's maximum bending stress. The cannula may have a stylet associated with it in order to facilitate access to a vertebral body or may be used over the wire intraoperatively. The plateau of the cannula can also be used to protect breached lateral walls from cement leakage.

In some embodiments, the system includes a scoop cannula configured to preferentially direct/inflate an inflatable bone tamp. The inflatable bone tamp is positioned within the scoop cannula such that the scoop of the scoop cannula is positioned under a balloon of the inflatable bone tamp to provide a backstop for the balloon to inflate against. The scoop is configured to direct the balloon to a specific area of a patient's anatomy, such as, for example, a vertebral body and/or prevent the balloon from expanding into an undesired location, such as, for example, a breached cortical shell or collapsed end plate. In some embodiments, the scoop may be configured to position the balloon adjacent to an end plate or a soft region of bone.

In some embodiments, the scoop cannula comprises a shape memory material. In some embodiments, the scoop cannula comprises a superelastic material. In some embodiments, the scoop cannula comprises super-elastic Nitinol. In some embodiments, the scoop cannula comprises any material that will deform elastically and then return to its original shape to minimize the effects of deformation.

In some embodiments, one or all of the components of the surgical system may be disposable, peel-pack, pre-packed sterile devices. In some embodiments, the components of the surgical system are configured for one-time use and are disposed after they are used one time. However, it is contemplated that one or all of the components of the surgical system may be reusable. The surgical system may be configured as a kit with multiple sized and configured components, including, for example, various scoop cannulas, balloons, etc. In some embodiments, one or more of the components of the surgical system are configured to be sterilized.

In some embodiments, the disclosed surgical system, kits and methods may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The system, kits and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment of" a disease or condition refers to performing a procedure to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-18, there are illustrated components of a surgical system 20 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Surgical system 20 includes a scoop cannula, such as, for example, kyphoplasty cannula 22. Cannula 22 includes a shaft 24 that extends along a longitudinal axis L between a first end surface 26 and an opposite second end surface 28. Shaft 24 comprises an inner surface 30 defining a lumen 32. Lumen 32 is coaxial with axis L and extends the entire length of shaft 24. Lumen 32 has a circular cross-sectional configuration and a uniform diameter along the entire length of lumen 32. In some embodiments, lumen 32 may have various cross section configurations, such as, for example, oval, oblong, triangular, rectangular, square, polygonal, irregular, uniform, non-uniform, variable, tubular and/or tapered. In some embodiments, lumen 32 may be disposed at alternate orientations, relative to axis L, such as, for example, transverse and/or other angular orientations such as acute or obtuse, co-axial and/or may be offset or staggered. Shaft 24 comprises a first opening 34 that extends through end surface 26 and a second opening 36 that extends through end surface 28. Openings 34, 36 are each in communication with lumen 32.

Cannula 22 includes a semicircular plateau, such as, for example, a scoop 38 extending from end surface 28 along axis L such that scoop 38 faces away from end surface 26. Scoop 38 includes an outer surface **38*a* that is continuous with an outer surface 24*a* of shaft 24. That is, there are no gaps or recesses between outer surface 24*a* and outer surface 38*a* such that outer surface 24*a* smoothly transitions into outer surface 38*a*. In some embodiments, outer surface 38*a* extends parallel to outer surface 24*a* and/or axis L along an entire length of scoop 38. In some embodiments, outer surface 38*a* may be disposed at alternate orientations, relative to outer surface 24*a*** and/or axis L, such as, for example, transverse, perpendicular and/or other angular orientations such as acute or obtuse, co-axial and/or may be offset or staggered.

Scoop 38 includes a center portion 40 that is positioned between side portions 42, 44 of scoop 38. Center portion 40 is configured to support a bottom surface of a balloon as the balloon is inflated such that the balloon expands away from scoop 38 and side portions 42, 44 are each configured to support a side surface of a balloon as the balloon is inflated to prevent the balloon from rolling over scoop 38 as the balloon is inflated, as discussed herein. In some embodiments, side portions 42, 44 are each tapered from end surface 28 to a distal end surface 52 of scoop 38. That is, side portions 42, 44 each have a height adjacent to end surface 28 that is greater than a height of side portions 42, 44 adjacent to distal end surface 52. In some embodiments, side portions 42, 44 are each continuously tapered from end surface 28 to a distal end surface 52 of scoop 38.

Side portion 42 includes a top surface 46 and side portion 44 includes a top surface 48. Scoop 38 includes an arcuate inner surface 50 that is continuous with inner surface 30 of shaft 24. That is, there are no gaps or recesses between inner surface 30 and arcuate inner surface 50 such that inner surface 30 smoothly transitions into arcuate inner surface 50. Arcuate inner surface 50 is configured to support a bottom surface of a balloon as the balloon is inflated to provide a backstop for the balloon to inflate against, as discussed herein. In some embodiments, arcuate inner surface 50 is concavely curved from top surface 46 to top surface 48. In some embodiments, arcuate inner surface 50 is continuously curved from top surface 46 to top surface 48. In some embodiments, arcuate inner surface 50 has a continuous radius of curvature from top surface 46 to top surface 48. In some embodiments, arcuate inner surface 50 has a radius of curvature from top surface 46 to top surface 48 that is equal to the radius of curvature of inner surface 30 of shaft 24. In some embodiments, arcuate inner surface 50 has a radius of curvature from top surface 46 to top surface 48 that is greater than the radius of curvature of inner surface 30 of shaft 24. In some embodiments, arcuate inner surface 50 has a radius of curvature from top surface 46 to top surface 48 that is less than the radius of curvature of inner surface 30 of shaft 24.

Scoop 38 includes a wrinkle, such as, for example, a rib 54 that extends outwardly from outer surface **38*a* of scoop 38 Rib 54 extends along at least a portion of center portion 40 of scoop 38. Rib 54 is configured to increase the stiffness of scoop 38 and provide additional support to cannula 22 to reduce the amount of plastic deformation that cannula 22 undergoes due to balloon inflation versus a cannula that does not include a wrinkle or rib. Rib 54 extends parallel to longitudinal axis L along an entire length of rib 54. Rib 54 is positioned between end surface 28 of shaft 24 and distal end surface 52 of scoop 38. In some embodiments, rib 54 is positioned equidistantly between end surface 28 of shaft 24 and distal end surface 52 of scoop 38. In some embodiments, rib 54 extends continuously along center portion 40 from end surface 28 to distal end surface 52. In some embodiments, rib 54 extends along at least a portion of shaft 24 and at least a portion of scoop 38. For example, it is envisioned that rib 54 can extend continuously from end surface 26 of shaft 24 to distal end surface 52** of scoop.

In some embodiments, rib 54 includes a concave inner surface **65*a* that is continuous with inner surface 50 of scoop 38 and a convex outer surface 65*b* that is continuous with outer surface 38*a* of scoop 38. Rib 54 has a thickness t1 that is defined by the distance from inner surface 65*a* to outer surface 65*b* and scoop 38 has a thickness t2 that is defined by the distance from inner surface 50 to outer surface 38*a*. In some embodiments, thickness t1 is uniform along an entire length and/or area of rib 54. In some embodiments, thickness t1 is equal to thickness t2. That is, scoop 38 may have a uniform thickness along an entire area of scoop 38, including the portion of scoop 38 that includes rib 54. In some embodiments, thickness t1 is greater than thickness t2. In some embodiments, thickness t1 is less than thickness t2. In some embodiments, rib 54 is curved from a first end 55*a*** of rib 54 to a second end 55*b* of rib 54. In some embodiments, inner surface 65*a* of rib 54 is concavely curved from first end 55*a* of rib 54 to second end 55*b* of rib 54 and outer surface 65*b* of rib 54 is convexly curved from first end 55*a* of rib 54 to second end 55*b* of rib 54. In some embodiments, rib 54 is continuously curved from first end 55*a* of rib 54 to second end 55*b* of rib 54. In some embodiments, side portions 42, 44 each have a radius of curvature that is greater than a radius of curvature of rib 54. In some embodiments, center portion 40 has a radius of curvature proximal and distal to rib 54 that is greater than a radius of curvature of rib 54. In some embodiments, rib 54 extends outwardly from arcuate inner surface 50 of scoop 38. In some embodiments, rib 54 extends only from outer surface 38*a* of scoop 38 and does not extend from arcuate inner surface 50 of scoop 38. In some embodiments, all or only a portion of rib 54 may be variously configured and dimensioned, such as, for example, planar, concave, polygonal, irregular, uniform, non-uniform, staggered, tapered, consistent or variable, depending on the requirements of a particular application. In some embodiments, rib 54 may be disposed at alternate orientations, relative to longitudinal axis L, such as, for example, transverse, perpendicular and/or other angular orientations such as acute or obtuse, co-axial and/or may be offset or staggered.

Figure 2:
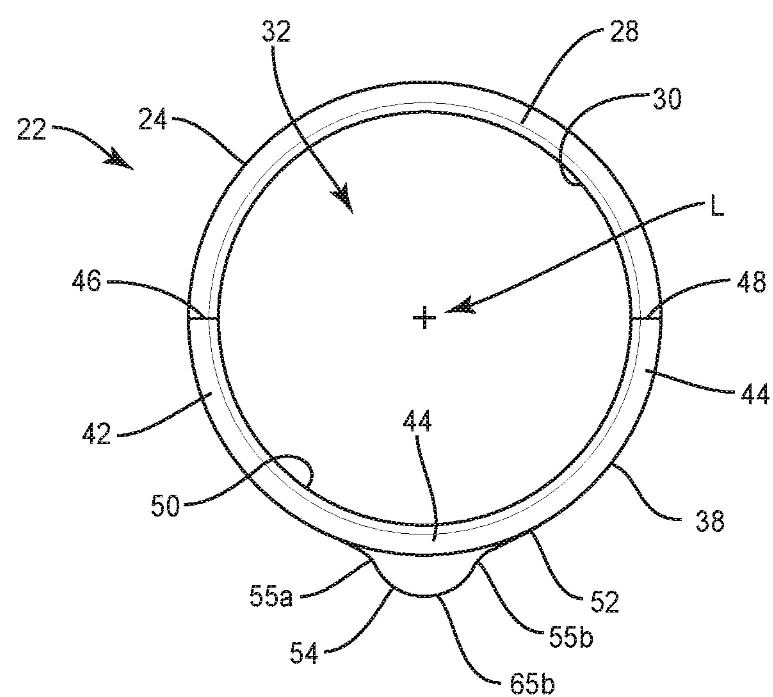
FIG. 2 is an end view of the component shown in FIG. 1.
Figure 3:
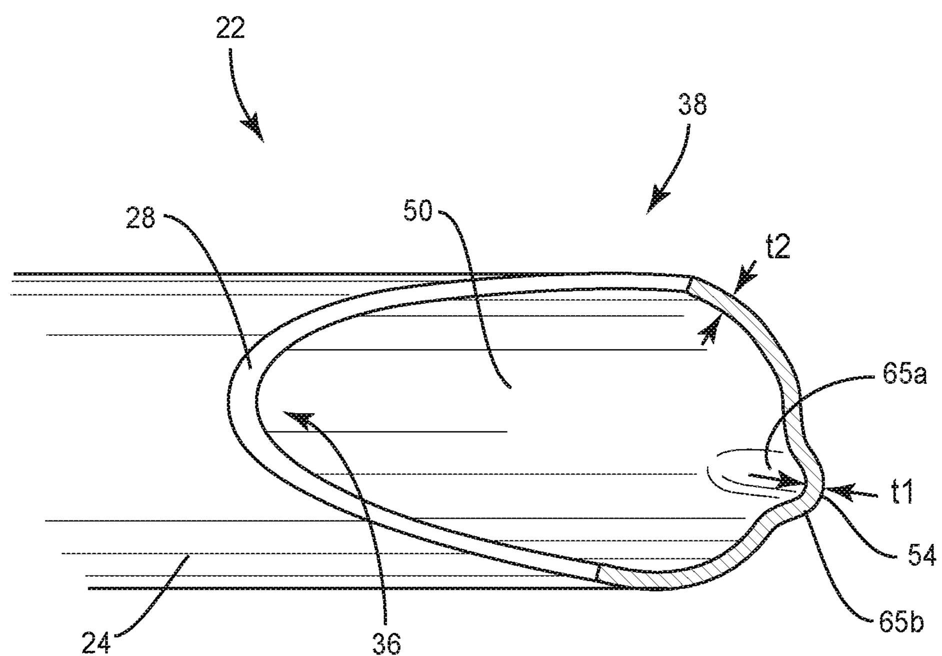
FIG. 3 is a cross sectional, perspective view of the component shown in FIG. 1, taken along lines III-III in FIG. 1.

In one embodiment, shown in FIGS. 1-3, cannula 22 includes only one rib 54. In some embodiments, cannula 22 may include a plurality of ribs 54. For example, in one embodiment, shown in FIGS. 4-6, cannula 22 includes three ribs 54. Ribs 54 are spaced apart from one another. A first rib 54*a* is positioned equidistantly between top surface 46 and top surface 48, a second rib 54*b* extends along side portion 42 and a third rib 54*c* extends along side portion 44. Scoop 38 is concavely curved between first rib 54*a* and second rib 54*b* and between first rib 54*a* and third rib 54*c*. Ribs 54*a*, 54*b*, 54*c* each extend parallel to longitudinal axis L. In some embodiments, rib 54*a*, rib 54*b* and/or rib 54*c* may be disposed at alternate orientations, relative to longitudinal axis L, such as, for example, transverse, perpendicular and/or other angular orientations such as acute or obtuse, co-axial and/or may be offset or staggered. It is envisioned that the plurality of ribs 54 may include two ribs 54, three ribs 54, four ribs 54, five ribs 54, six ribs 54, seven ribs 54, eight ribs 54, nine ribs 54, ten ribs 54, eleven ribs 54, twelve ribs 54, thirteen ribs 54, fourteen ribs 54, fifteen ribs 54, sixteen ribs 54, seventeen ribs 54, eighteen ribs 54, nineteen ribs 54, twenty ribs 54, or more than twenty ribs 54. The plurality of ribs 54 may all have the same shape or may have different shapes. In some embodiments, each of the plurality of ribs 54 extend parallel to one another. In some embodiments, at least one of the plurality of ribs 54 extends transverse to at least one of the other ribs 54. In some embodiments, each of the plurality of ribs 54 has the same length. In some embodiments, at least one of the plurality of ribs 54 has a length that is different than a length of at least one of the other ribs 54.

In some embodiments, shaft 24 and/or scoop 38 are made from a shape memory material. In some embodiments, shaft 24 and/or scoop 38 are made from a superelastic material. In some embodiments, shaft 24 and/or scoop 38 are made from super-elastic Nitinol. In some embodiments, shaft 24 and/or scoop 38 are made from a material that will deform elastically and then return to its original shape to minimize the effects of deformation. For example, shaft 24 and/or scoop 38 are made from super-elastic Nitinol such that side portions 42, 44 will deflect relative to center portion 40 when the balloon is inflated and then return to their original shape after the balloon is deflated.

Figure 8:
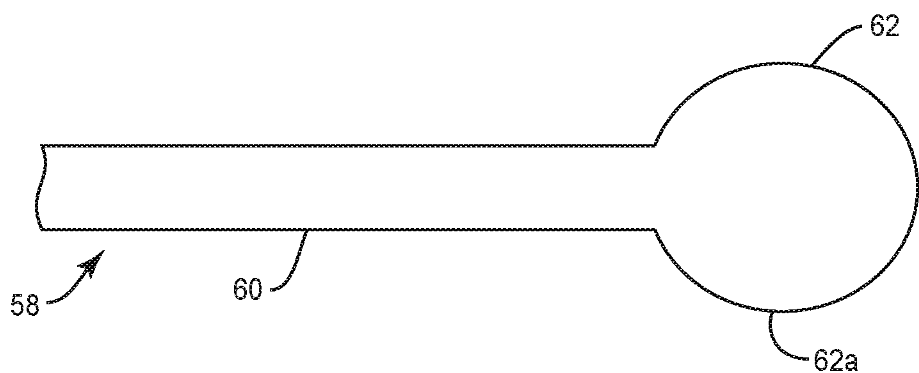
FIG. 8 is a side, cross sectional view of the component shown in FIG. 7.
Figure 9:
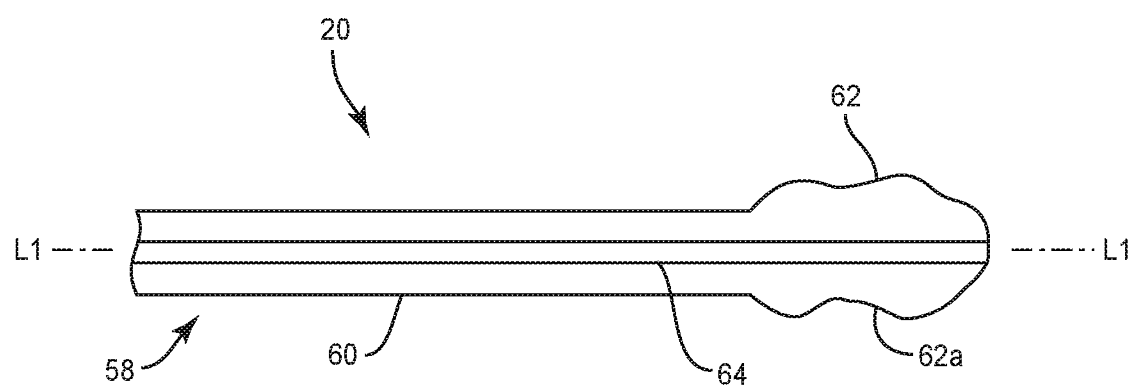
FIG. 9 is a side, cross sectional view of a component of the surgical system, in accordance with the present principles of the present disclosure.
Figure 10:
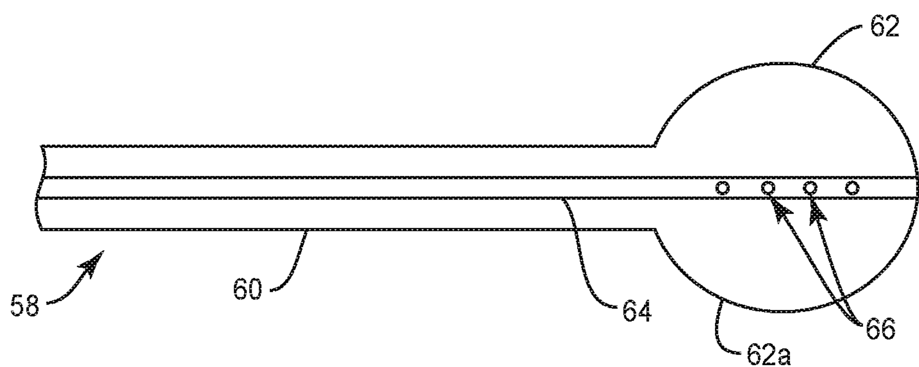
FIG. 10 is a side, cross sectional view of the component shown in FIG. 9.

System 20 includes a balloon catheter, such as, for example, an inflatable bone tamp 58. In one embodiment, shown in FIGS. 5 and 6, inflatable bone tamp 58 includes an outer tube, such as, for example, a tube 60 and a balloon 62 that is coupled to an end of tube 60. An inflation material, such as, for example, air, saline, or a contrast solution may be delivered through tube 60 and into balloon 62 to move balloon 62 from an uninflated orientation shown in FIG. 7 to an inflated orientation shown in FIG. 8. In one embodiment, shown in FIGS. 9 and 10, inflatable bone tamp 58 includes an inner tube, such as, for example a tube 64 positioned within tube 60. A first end of balloon 62 is coupled to an end of tube 60. In some embodiments, an inflation material, such as, for example, air, saline, or a contrast solution may be delivered through the space between tube 60 and tube 64 and into balloon 62 to move balloon 62 from an uninflated orientation shown in FIG. 9 to an inflated orientation shown in FIG. 10. In some embodiments, tube 64 includes one or a plurality of apertures 66 such that an inflation material, such as, for example, air, saline, or a contrast solution may be delivered through tube 64 and into balloon 62 through apertures 66 to move balloon 62 from an uninflated orientation shown in FIG. 9 to an inflated orientation shown in FIG. 10. In some embodiments, balloon 62 is configured to expand radially about a longitudinal axis L1 defined by tube 60, as shown in FIGS. 8 and 10. In some embodiments, balloon 62 may configured to expand in only one direction. For example, balloon 62 may be made such that a top portion of balloon 62 is thicker or comprises a different material than a bottom portion of balloon 62 such that the bottom portion of balloon 62 will expand more than the top portion of balloon 62 when balloon 62 is inflated.

Figure 11:
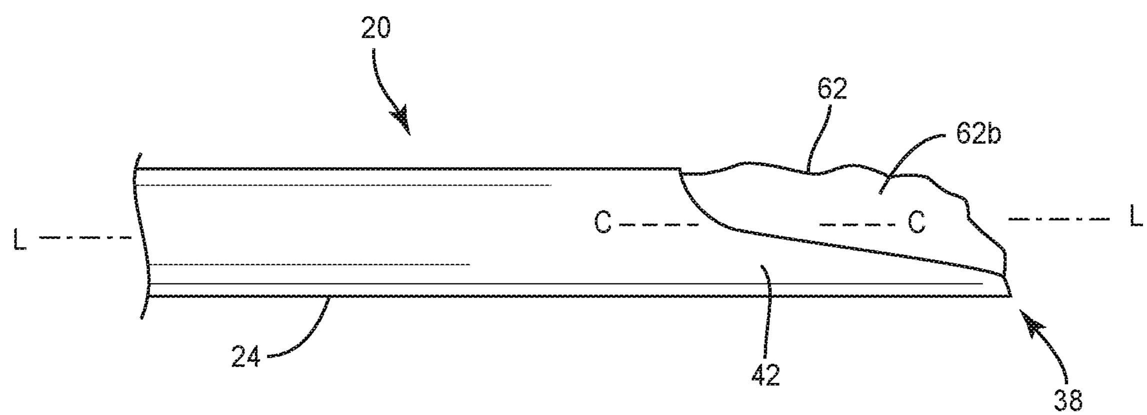
FIG. 11 is a side view of the components shown in FIGS. 1 and 7.
Figure 12:
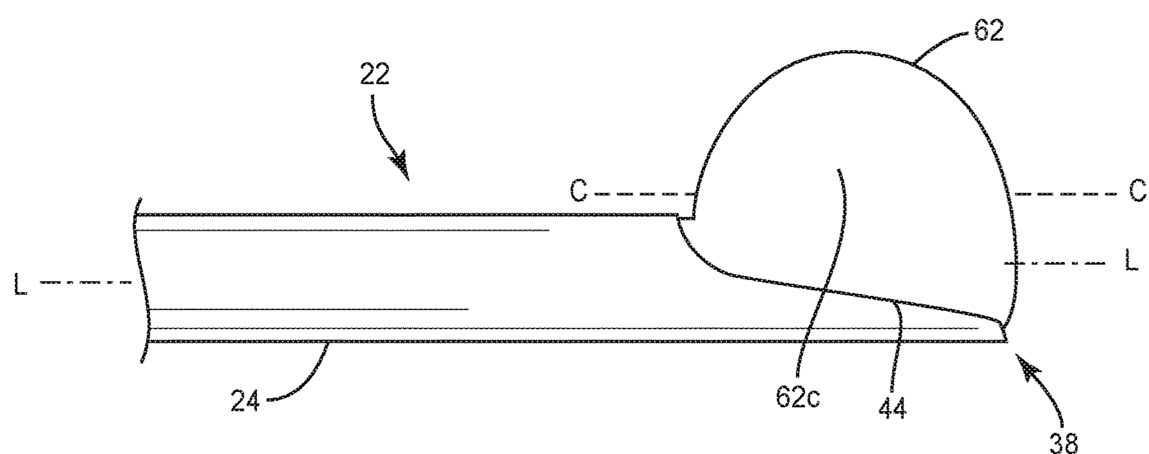
FIG. 12 is a side view of the components shown in FIGS. 1 and 7.

Inflatable bone tamp 58 is configured for insertion into cannula 22 such that tube 60 is positioned within lumen 32 of shaft 24 and balloon 62 is positioned within scoop 38, as shown in FIGS. 11 and 12. In some embodiments, axis L is coaxial with axis L1 when inflatable bone tamp 58 is inserted into cannula 22. When balloon 62 is positioned within scoop 38, a bottom surface 62*a* of balloon 62 directly engages arcuate inner surface 50, a first side surface 62*b* of balloon 62 directly engages side portion 42 and an opposite second side surface 62*c* of balloon 62 directly engages side portion 44. As balloon 62 moves from the uninflated orientation to the inflated orientation, arcuate inner surface 50 supports bottom surface 62*a* of balloon 62 as balloon 62 is inflated to provide a backstop for balloon 62 to inflate against such that balloon 62 expands away from arcuate inner surface 50. Because balloon 62 expands away from scoop 38, a centerline C of balloon 62 is offset from axis L when balloon 62 is inflated, as shown in FIG. 12. In some embodiments, centerline C of balloon 62 may be coaxial with axis L when balloon 62 is uninflated, as shown in FIG. 11. Side portion 42 of scoop 38 supports side surface 62*b* of balloon 62 and side portion 44 of scoop 38 supports side surface 62*c* of balloon as balloon 62 moves from the uninflated orientation to the inflated orientation to prevent balloon 62 from rolling over scoop 38 as balloon 62 is inflated.

In operation and use, to treat a bone disorder, such as, for example, a spinal fracture, a medical practitioner obtains access to a target location including at least one bony structure, such as, for example, a fractured vertebra V, in any appropriate manner, such as through incision and retraction of tissue. It is envisioned that the surgical system 20 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Figure 13:
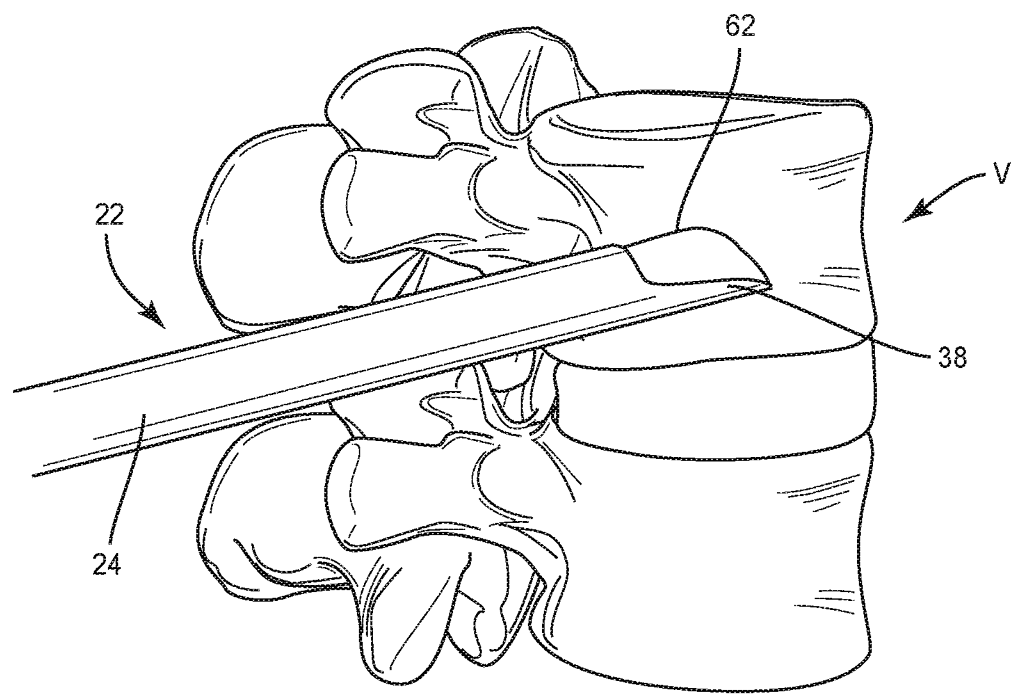
FIG. 13 is a plan view of the components shown in FIGS. 1 and 7.
Figure 14:
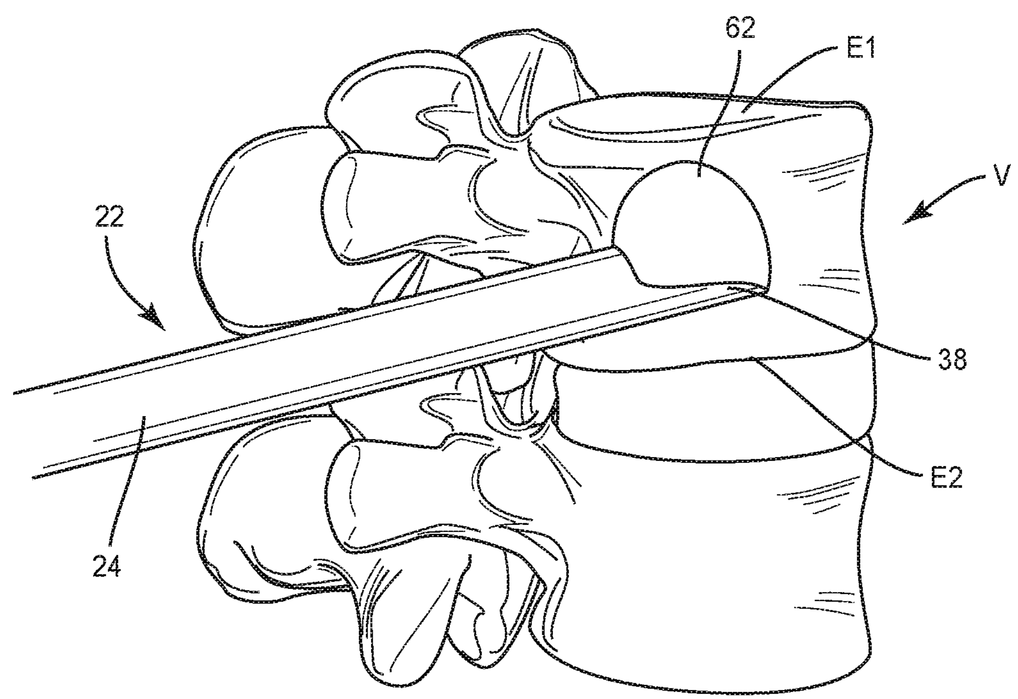
FIG. 14 is a plan view of the components shown in FIGS. 1 and 7.
Figure 15:
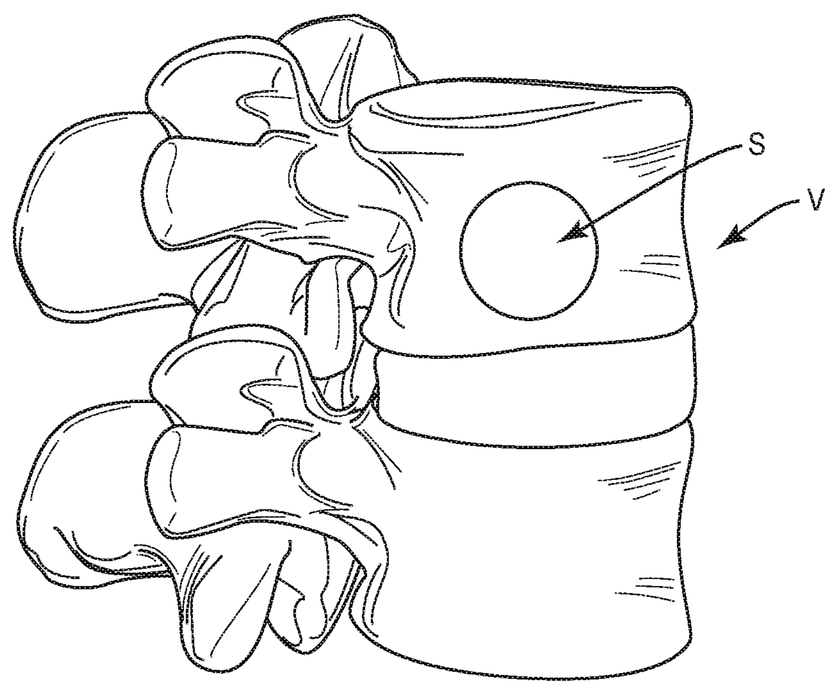
FIG. 15 is a plan view of a surgical site.

Inflatable bone tamp 58 is inserted into cannula 22 such that tube 60 is positioned within lumen 32 of shaft 24 and balloon 62 is positioned within scoop 38. Scoop 38 and balloon 62 are inserted into a vertebral body of vertebra V with balloon 62 in the uninflated orientation, as shown in FIG. 13. Balloon 62 is then moved from the uninflated orientation to the inflated orientation, as shown in FIG. 14. As balloon 62 moves from the uninflated orientation to the inflated orientation, arcuate inner surface 50 of scoop 38 supports bottom surface 62*a* of balloon 62 as balloon 62 is inflated to provide a backstop for balloon 62 to inflate against such that balloon 62 expands away from arcuate inner surface 50. This allows a medical practitioner to direct balloon 62 to a selected portion of vertebra V. For example, scoop 38 may be used to direct balloon 62 toward a wall of an endplate E1 of vertebra V, as shown in FIG. 14. That is, rather than allow balloon 62 to expand radially about axis L, scoop 38 causes balloon 62 to expand more toward endplate E1 than toward an endplate E2 of vertebra V. As discussed herein, scoop 38 helps to distribute the load created by balloon 62 against vertebra V to increase the lifting force of balloon 62. As balloon 62 moves from the uninflated orientation to the inflated orientation, balloon 62 creates a void space S within vertebra V. Balloon 62 is moved from the inflated orientation to the uninflated orientation and cannula 22 is removed from vertebra V, leaving void space S, as shown in FIG. 15.

Figure 16:
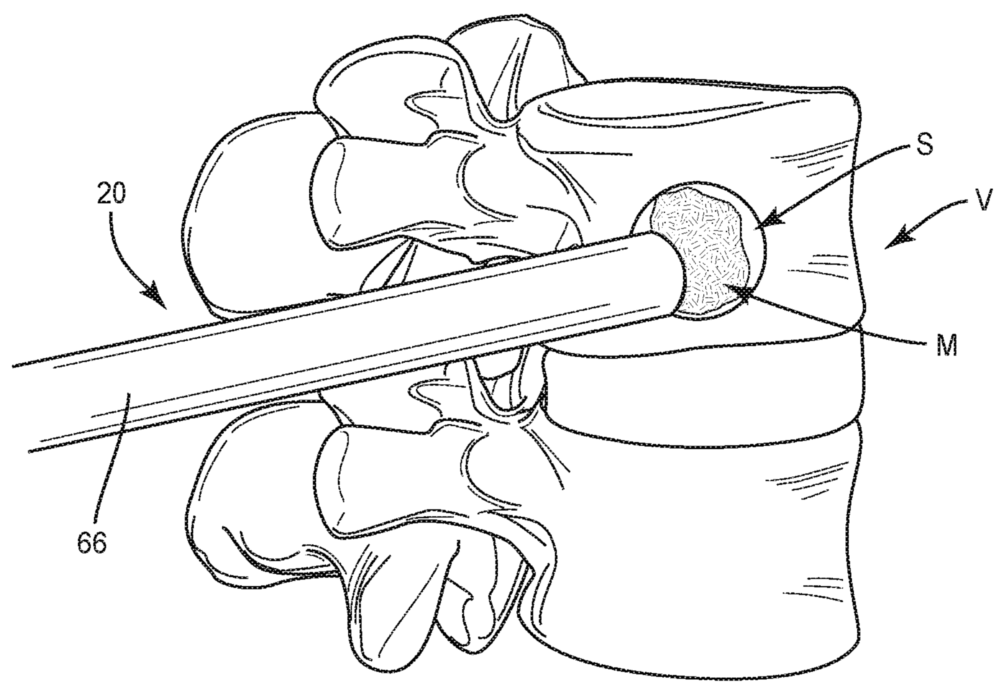
FIG. 16 is a plan view of a component of the surgical system, in accordance with the present principles of the present disclosure.

System 20 includes a second cannula 66 that is inserted into vertebra V such that an end of the cannula is positioned within void space S, as shown in FIG. 16. A material M may be delivered through cannula 66 and into void space S to fill all or a portion of void space S with material M. In some embodiments, material M is a curable bone filler material, such as, for example, bone cement. Material M then cures within vertebra V to treat the fracture by reducing pain from the fracture, stabilizing vertebra V and/or restoring vertebra V back to its normal height.

In some embodiments, a kit containing one or more components of surgical system 20 is provided. The kit may comprise components from any of the embodiments discussed herein. In some embodiments, the kit comprises one or a plurality of trocar stylets having the same or different sizes, lengths or shapes, one or a plurality of scoop cannulas, such as, for example, cannulas 22, cannulas 66 and/or cannulas 68 having different sizes, lengths or shapes, and one or a plurality of position indicators having the same or different sizes, lengths or shapes. In some embodiments, the kit comprises a plurality of cannulas, such as, for example, cannulas 22 having scoops 38 with different widths and/or lengths configured for use with different size balloons. In some embodiments, the kit comprises one or more of the inflation materials discussed herein. In some embodiments, the kit comprises one or more bone filler materials, such as, for example, material M.

EXAMPLE

Figure 4:
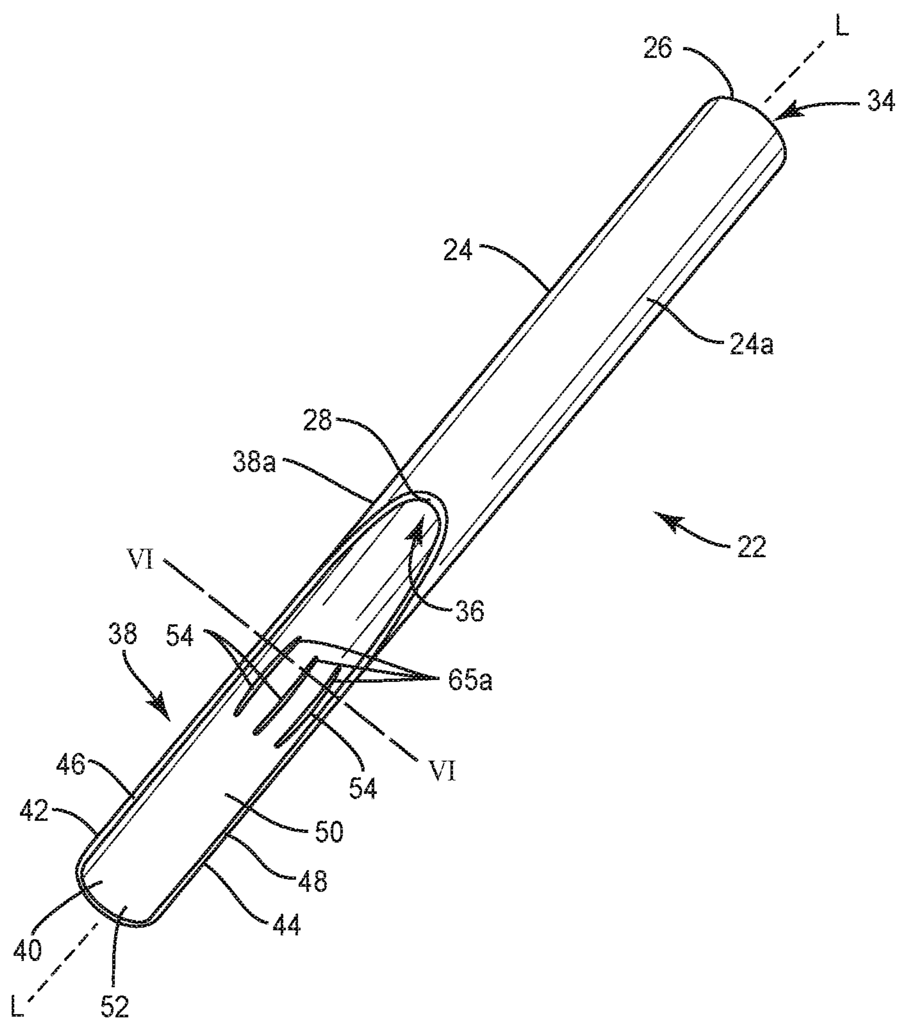
FIG. 4 is a perspective view of one embodiment of a component of the surgical system, in accordance with the present principles of the present disclosure.
Figure 5:
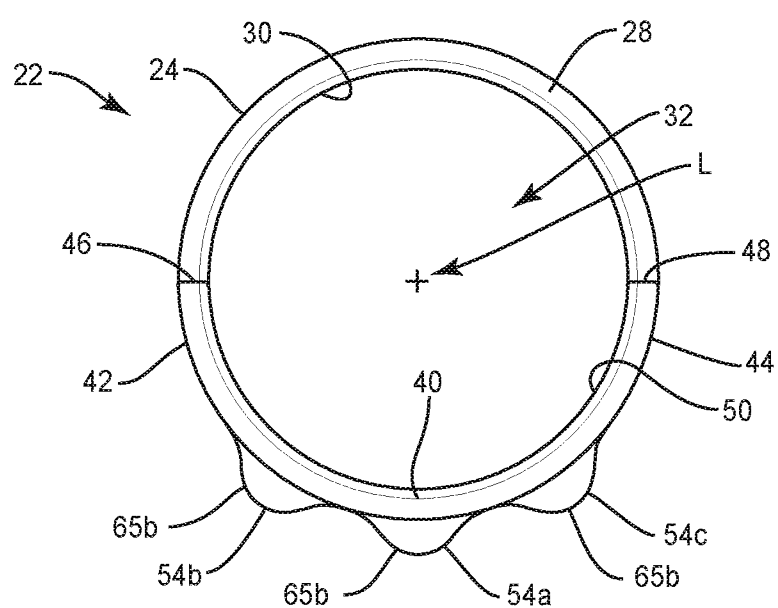
FIG. 5 is an end view of the component shown in FIG. 3.
Figure 6:
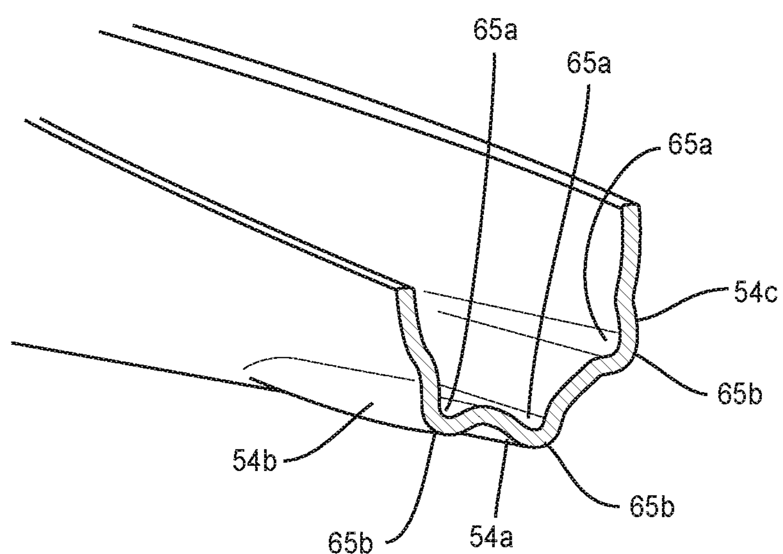
FIG. 6 is a cross sectional, perspective view of the component shown in FIG. 1, taken along lines VI-VI in FIG. 4.
Figure 7:
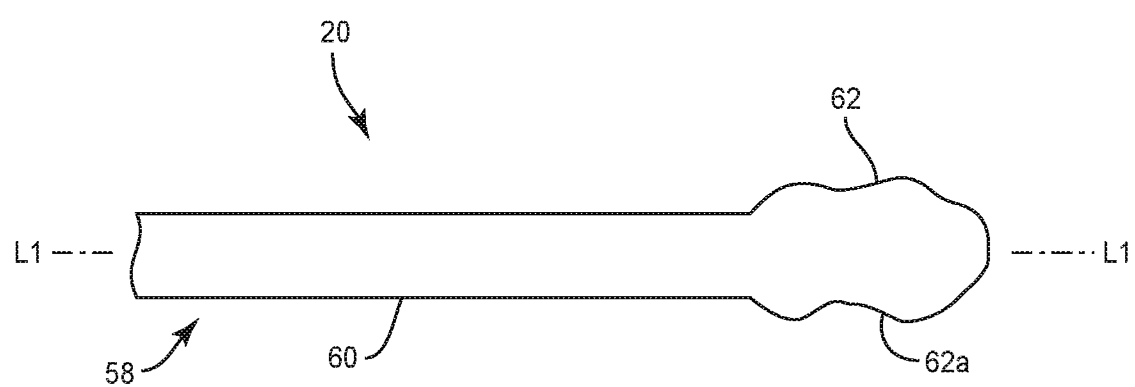
FIG. 7 is a side, cross sectional view of a component of the surgical system, in accordance with the present principles of the present disclosure.
Figure 17:
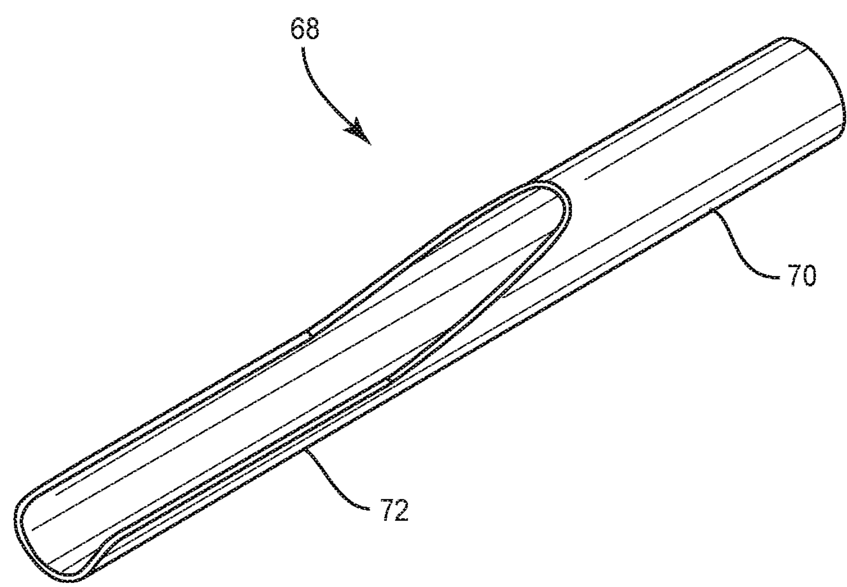
FIG. 17 is a perspective view of a cannula.

To demonstrate that scoop cannulas that include one or more wrinkle or rib, such as, for example, rib 54 increases the stiffness of the scoop and provides additional support to the cannula to reduce the amount of plastic deformation that the cannula undergoes due to balloon inflation versus a cannula that does not include a wrinkle or rib, Applicant has tested a scoop cannula without any ribs, a scoop cannula with one rib and a scoop cannula with three ribs to determine the equivalent plastic strain of each of the cannulas. A cannula 68 is shown in FIG. 17. Cannula 68 is similar to cannula 22 and includes a shaft 70 similar to shaft 24 and a scoop 72 similar to scoop 38 that is coupled to shaft 70. Shaft 70 has the same size and shape as shaft 24 and is made of the same material(s). Scoop 72 has the same size and shape as scoop 38 and is made of the same material(s). Cannula 68 differs from cannula 22 shown in FIGS. 1-3 and cannula 22 shown in FIGS. 4-6 in that cannula 68 does not include a wrinkle or rib, such as, for example, rib(s) 54. Inflatable bone tamp 58 was inserted into each of cannula 68, cannula 22 shown in FIGS. 1-3 and cannula 22 shown in FIGS. 4-6 such that balloon 62 was positioned within scoop 38 or scoop 72. Balloon 62 was then moved from the uninflated configuration to the inflated configuration. As balloon 62 moved from the uninflated configuration to the inflated configuration, balloon 62 pressed against scoop 38 or scoop 72. The deflection of scoop 38 and scoop 72 was measured. The medium used for testing was 5.0 PCF saw-bone solid rigid. As shown in FIG. 18, cannula 68 exhibited 0.0392365 in/in of strain; cannula 22 shown in FIGS. 1-3 exhibited 0.13139 in/in of strain; and cannula 22 shown in FIGS. 4-6 exhibited 0.0087888 in/in of strain. That is, scoop 38 of cannula 22 shown in FIGS. 1-3 is stiffer than scoop 72 of cannula 68 and scoop 38 of cannula 22 shown in FIGS. 4-6 is stiffer than scoop 38 of cannula 22 shown in FIGS. 1-3. This demonstrates that ribs 54 provide additional support to cannula 22 to reduce the amount of plastic deformation that cannula 22 undergoes due to balloon inflation versus a cannula that does not include a wrinkle or rib (e.g., cannula 68). This demonstrates that a plurality of ribs 54 provide additional support to cannula 22 versus cannulas 22 that include only one rib 54.

Figure 19:
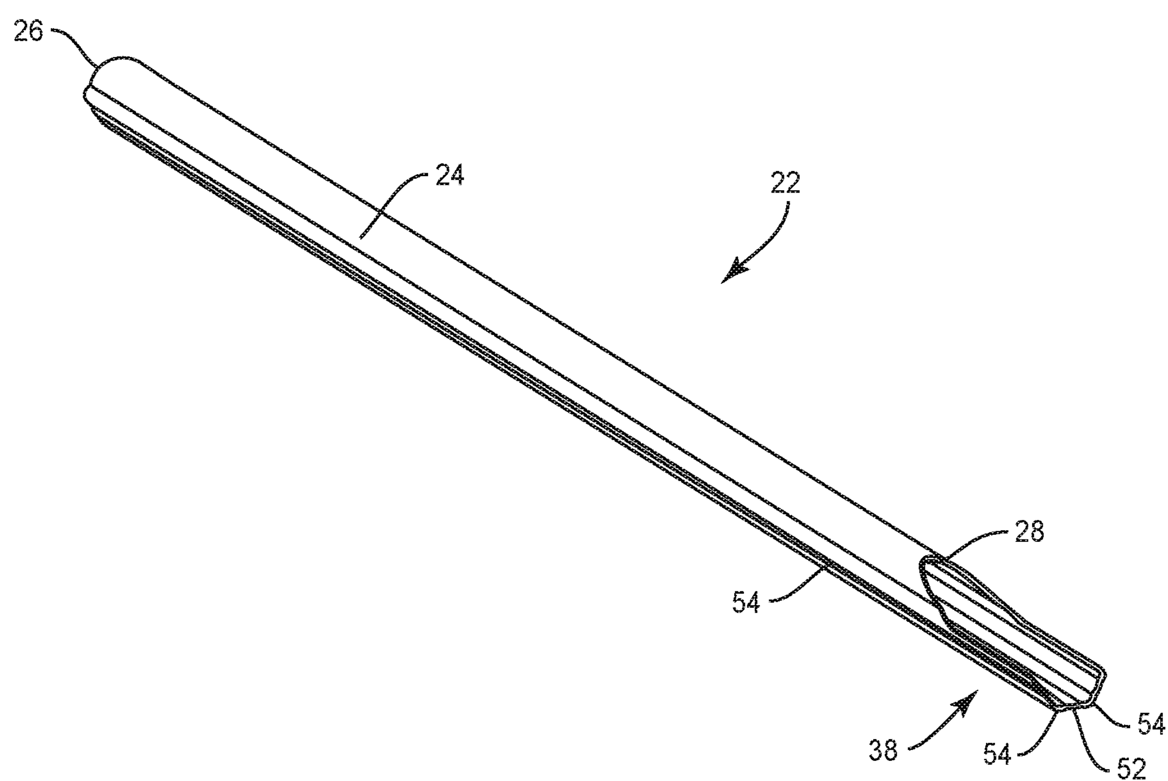
FIG. 19 is a side, perspective view of one embodiment of a component of the surgical system, in accordance with the present principles of the present disclosure.
Figure 20:
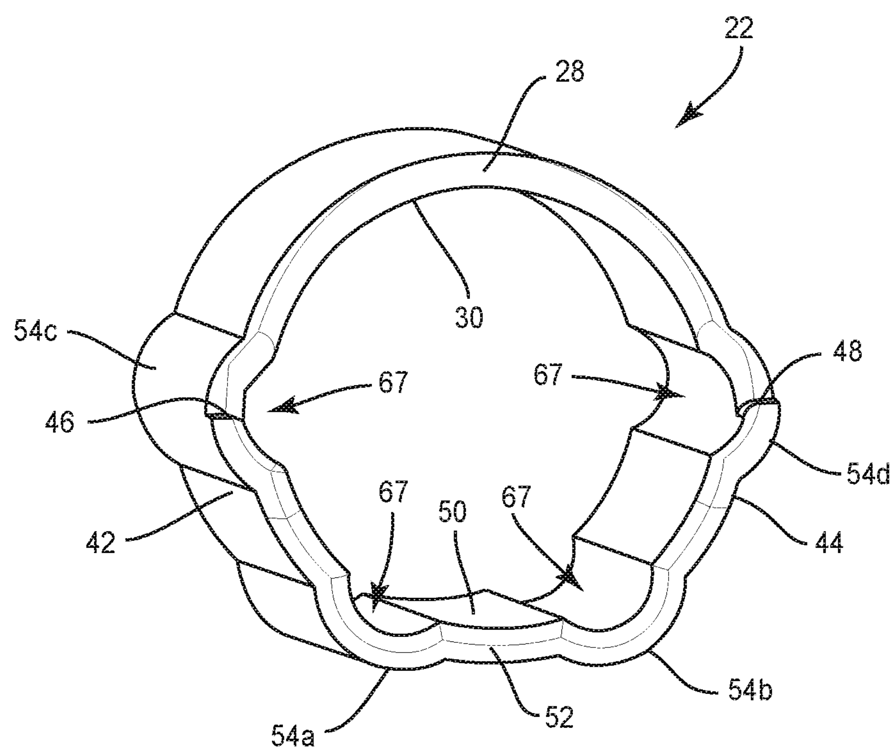
FIG. 20 is an end, perspective view of the component shown in FIG. 22.
Figure 21:
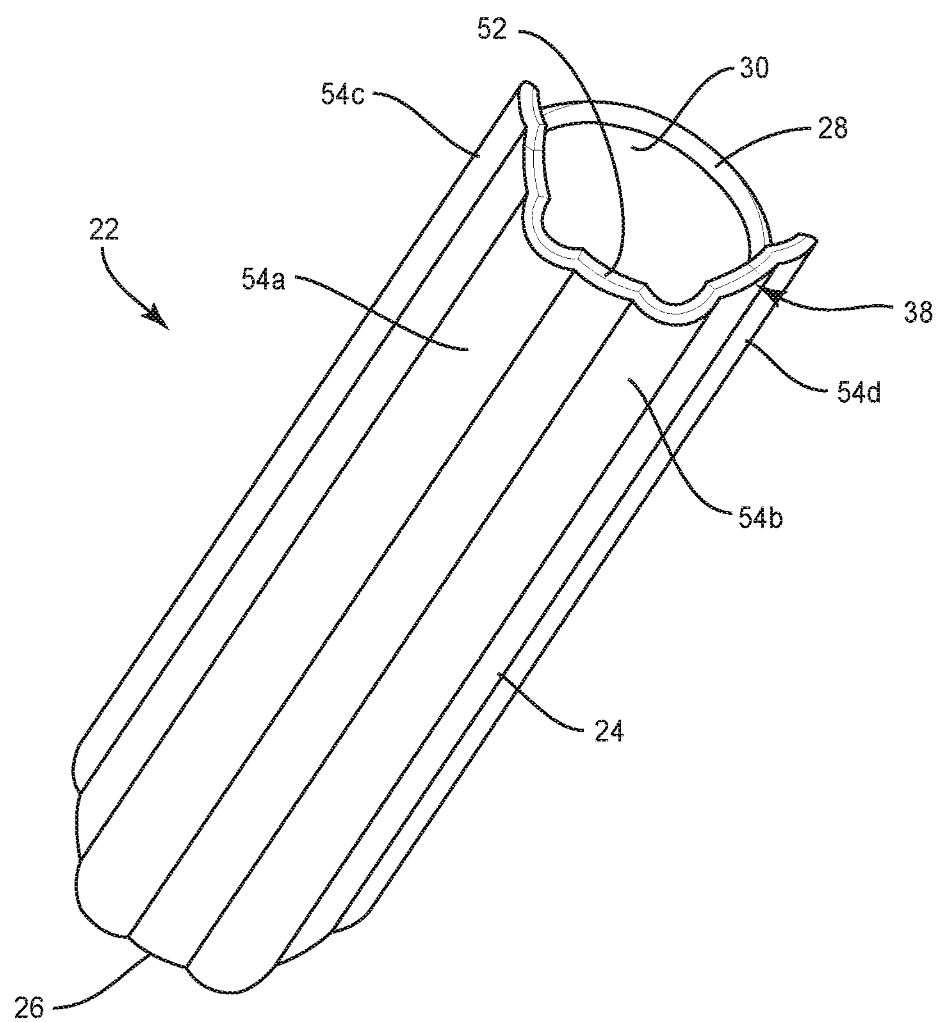
FIG. 21 a bottom, perspective view of the component shown in FIG. 22.

In some embodiments, shown in FIGS. 1-6, ribs 54 extend only along scoop 38. That is, ribs 54 do not extend along any portion of shaft 24 and/or are spaced apart from shaft 24. In some embodiments, cannula 22 includes one or a plurality of ribs 54 wherein ribs 54 extend along at least a portion of shaft 24. For example, in one embodiment, shown in FIGS. 19-21, ribs 54 extend continuously along shaft 24 and scoop 38. In one embodiment, ribs 54 extend along a portion of shaft 24 between end surface 26 and end surface 28. In one embodiment, ribs 54 extend from end surface 26 of shaft 24 to end surface 52 of scoop 38. In one embodiment, ribs 54 extend continuously along shaft 24 and scoop 38 such that there is no gap in ribs 54 between shaft 24 and scoop 38. It is envisioned that cannula 22 may include one or a plurality of ribs 54 that extend continuously along shaft 24 and scoop 38. As shown in FIGS. 20-21, cannula 22 includes a first rib 54*a* and a second rib 54*b* that are each positioned between side portions 42, 44 of scoop 38. Cannula 22 includes a third rib 54*c* that extends through side portion 42 and a fourth rib 54*d* that extends through side portion 44. Ribs 54*a*, 54*b*, 54*c*, 54*d* each extend parallel to axis L along an entire length of each of ribs 54. That is, ribs 54*a*, 54*b*, 54*c*, 54*d* each extend continuously from end surface 26 of shaft 24 to end surface 52 of scoop 38. As shown in FIGS. 20-21, ribs 54*a*, 54*b* each have a uniform width from end surface 26 of shaft 24 to end surface 52 of scoop 38. Ribs 54*c*, 54*d* each have a uniform width from end surface 26 of shaft 24 to end surface 28 of shaft 24 and a reduced width from end surface 28 to end surface 52. In some embodiments, the width of ribs 54*c*, 54*d* from end surface 28 to end surface 52 is half the width of ribs 54*c*, 54*d* from end surface 26 to end surface 28. In some embodiments, the width of ribs 54*c*, 54*d* from end surface 28 to end surface 52 is less than half the width of ribs 54*c*, 54*d* from end surface 26 to end surface 28. In some embodiments, the width of ribs 54*c*, 54*d* from end surface 28 to end surface 52 is more than half the width of ribs 54*c*, 54*d* from end surface 26 to end surface 28. In one embodiment, ribs 54*a*, 54*b*, 54*c*, 54*d* extend into inner surfaces 30, 50 of shaft 24 and scoop 38 such that ribs 54*a*, 54*b*, 54*c*, 54*d* each defines a cavity 67 that extends into inner surfaces 30, 50 of shaft 24 and scoop 38, as shown in FIG. 20. In some embodiments, all or only cavities 67 may be variously configured and dimensioned, such as, for example, planar, concave, polygonal, irregular, uniform, non-uniform, staggered, tapered, consistent or variable, depending on the requirements of a particular application.

Figure 22:
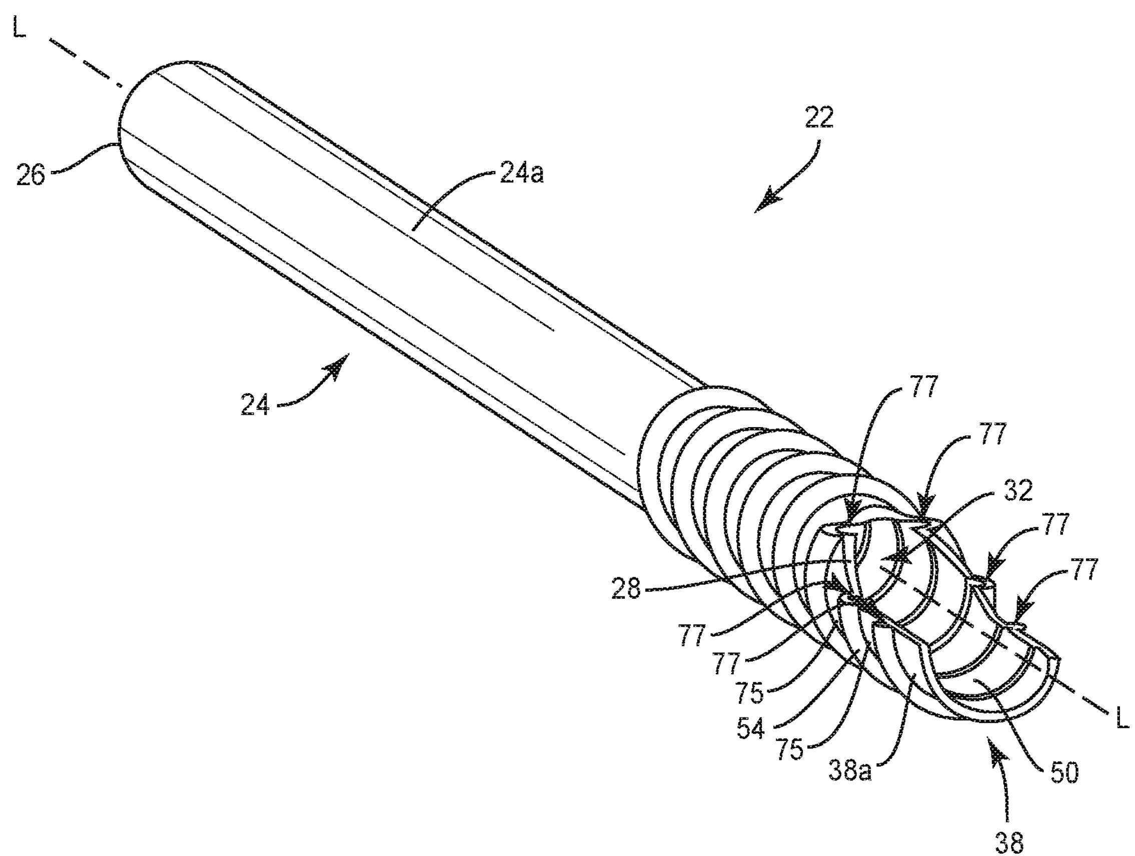
FIG. 22 is a side, perspective view of one embodiment of a component of the surgical system, in accordance with the present principles of the present disclosure.
Figure 23:
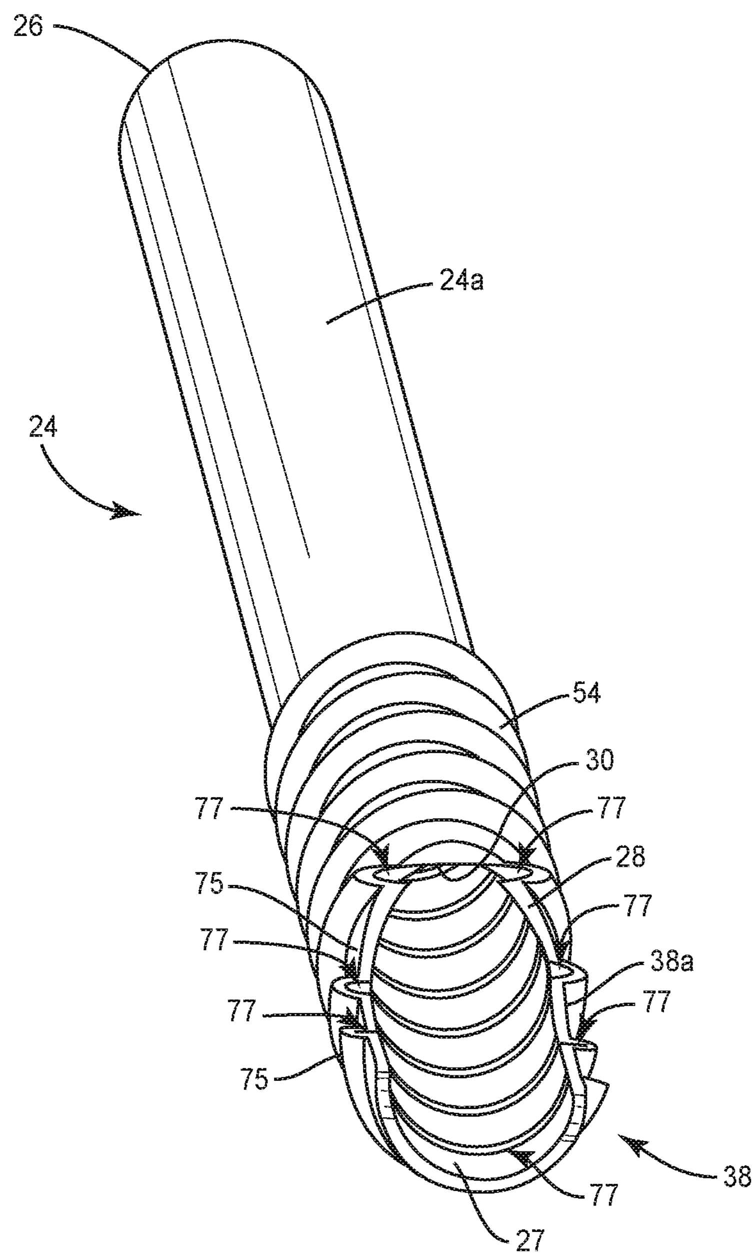
FIG. 23 is an end, perspective view of the component shown in FIG. 19.
Figure 24:
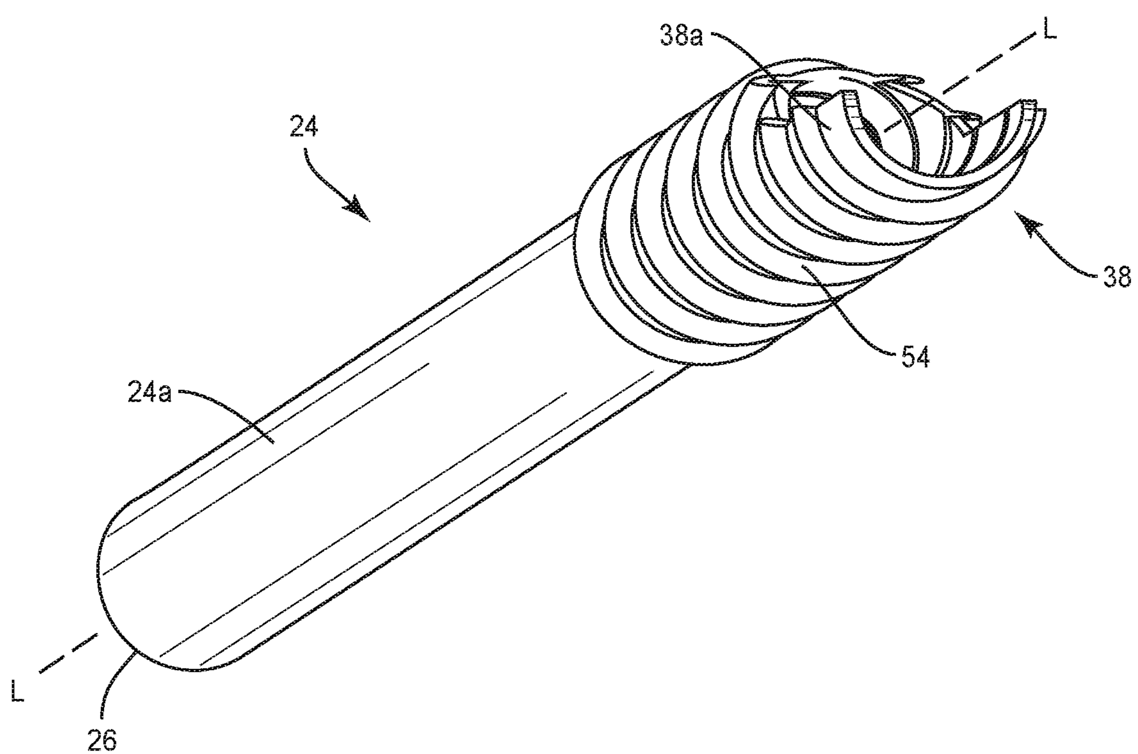
FIG. 24 is a bottom, perspective view of the component shown in FIG. 19.

In some embodiments, shown in FIGS. 1-6 and 19-21, ribs 54 extend parallel to axis L. In some embodiments, cannula 22 includes one or a plurality of ribs 54 wherein ribs 54 extend transverse to axis L along at least a portion of cannula 22. For example, in one embodiment, shown in FIGS. 22-24, cannula 22 includes a helical rib 54. That is, rib 54 extends helically about axis L from outer surface 38*a* of scoop 38. In one embodiment, rib 54 extends only along scoop 38. That is, rib 54 does not extend along shaft 24. In one embodiment, rib 54 extends along a portion of shaft 24 between end surface 26 and end surface 28, as shown in FIG. 22. In one embodiment, rib 54 extends continuously from outer surface 24*a* of shaft 24 and outer surface 38*a* of scoop 38 such that there is no gap in rib 54 between shaft 24 and scoop 38. In one embodiment, rib 54 extends continuously along outer surface 24*a* of shaft and includes spaced apart sections 75 that extend helically from outer surface 38*a* of scoop 38, as shown in FIG. 22. In one embodiment, rib 54 extends along an entire length of shaft 24 from end surface 26 to end surface 28. In one embodiment, inner surfaces 30, 50 of shaft 24 and scoop 38 are even and/or smooth such that there are no gaps or openings that extend into and/or through inner surfaces 30, 50. In one embodiment, rib 54 extends into inner surfaces 30, 50 of shaft 24 and scoop 38 such that rib 54 defines cavities 77 that extend into inner surfaces 30, 50 of shaft 24 and scoop 38, as shown in FIGS. 22 and 23. In some embodiments, all or only cavities 77 may be variously configured and dimensioned, such as, for example, planar, concave, polygonal, irregular, uniform, non-uniform, staggered, tapered, consistent or variable, depending on the requirements of a particular application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A cannula for kyphoplasty, the cannula comprising:

a shaft extending along a longitudinal axis between opposite first and second end surfaces, the shaft comprising an inner surface defining a lumen, the shaft comprising a first opening that extends through the first end surface and a second opening that extends through the second end surface; and a scoop comprising opposite first and second side walls each extending from the second end surface, the first side wall including a first top surface, the second side wall including a second top surface, the top surfaces extending parallel to one another along at least a portion of the scoop, the scoop comprising an arcuate inner surface that is continuous with the inner surface of the shaft and an opposite outer surface, the scoop having a maximum width, the maximum width being equal to a maximum width of the shaft, the scoop including a first portion, a second portion and a third portion between the first portion and the second portion, the third portion including a rib having a radius of curvature that is less than a radius of curvature of the first portion or the second portion, the rib extending parallel to the longitudinal axis and comprising a concave inner surface that is continuous with the arcuate inner surface and a convex outer surface that is continuous with the outer surface, the rib being spaced apart from the second top surface, the scoop having only one rib, a portion of the arcuate inner surface between the second end surface and the rib having a continuous radius of curvature from the first top surface to the second top surface.

2. A cannula as recited in claim 1, wherein the rib is positioned equidistant between the first and second side surfaces.

3. A cannula as recited in claim 1, wherein the arcuate inner surface is positioned between the top surfaces.

4. A cannula as recited in claim 1, wherein the shaft and the scoop comprise super-elastic nitinol.

5. A kyphoplasty kit comprising:

the cannula recited in claim 1;

a balloon catheter;

a stylet; and a position indicator.

6. A kyphoplasty kit as recited in claim 5, wherein the balloon catheter comprises a tube and a balloon that is coupled to an end of the tube.

7. A kyphoplasty kit as recited in claim 5, wherein the balloon catheter comprises:

an outer tube;

an inner tube positioned within the outer tube; and a balloon having a first end that is coupled to the outer tube and a second end that is coupled to the inner tube.

8. A kyphoplasty kit as recited in claim 5, wherein the balloon catheter includes a tube that is positioned within the lumen and a balloon that is coupled to an end of the tube such that the balloon directly engages the scoop.

9. A kyphoplasty kit as recited in claim 8, wherein the balloon has a maximum diameter when the balloon is in an inflated orientation that is greater than a maximum diameter of the lumen.

10. A cannula as recited in claim 1, wherein the first and second portions each have a first thickness defined by a distance from the arcuate inner surface to the outer surface and the third portion has a second thickness defined by a distance from the arcuate inner surface to the outer surface, the second thickness being equal to the first thickness.

11. A cannula as recited in claim 1, wherein the first and second portions each have a first thickness defined by a distance from the arcuate inner surface to the outer surface and the third portion has a second thickness defined by a distance from the arcuate inner surface to the outer surface, the second thickness being greater than the first thickness.

12. A cannula as recited in claim 1, wherein the first and second portions each have a first thickness defined by a distance from the arcuate inner surface to the outer surface and the third portion has a second thickness defined by a distance from the arcuate inner surface to the outer surface, the second thickness being less than the first thickness.

13. A cannula as recited in claim 1, wherein the top surfaces lie in a plane, the plane containing the longitudinal axis.

14. A cannula as recited in claim 1, wherein:

the top surfaces lie in a plane, the plane containing the longitudinal axis; and the first and second portions each have a first thickness defined by a distance from the arcuate inner surface to the outer surface and the third portion has a second thickness defined by a distance from the arcuate inner surface to the outer surface, the second thickness being greater than the first thickness.

15. A cannula as recited in claim 1, wherein:

the top surfaces lie in a plane, the plane containing the longitudinal axis; and the first and second portions each have a first thickness defined by a distance from the arcuate inner surface to the outer surface and the third portion has a second thickness defined by a distance from the arcuate inner surface to the outer surface, the second thickness being less than the first thickness.

16. A cannula as recited in claim 1, wherein:

the arcuate inner surface is positioned between the top surfaces; and the shaft and the scoop comprise super-elastic nitinol.

17. A cannula for kyphoplasty, the cannula comprising:

a shaft extending along a longitudinal axis between opposite first and second end surfaces, the shaft comprising an inner surface defining a lumen, the shaft comprising a first opening that extends through the first end surface and a second opening that extends through the second end surface; and a scoop extending from the second end surface, the scoop comprising an arcuate inner surface that is continuous with the inner surface of the shaft and an opposite outer surface, the scoop including opposite first and second side walls that each extend from the second end surface, the first side wall including a first top surface, the second side wall including a second top surface, the top surfaces lying in a plane, the plane containing the longitudinal axis, the scoop having a maximum width, the maximum width being equal to a maximum width of the shaft, the scoop including only one rib, the rib extending outwardly from the outer surface, the rib extending parallel to the longitudinal axis, the rib being positioned equidistant between the first and second top surfaces, the rib being spaced apart from the second top surface, a portion of the arcuate inner surface between the second end surface and the rib having a continuous radius of curvature from the first top surface to the second top surface.

18. A cannula for kyphoplasty, the cannula comprising:

a shaft extending along a longitudinal axis between opposite first and second end surfaces, the shaft comprising an inner surface defining a lumen, the shaft comprising a first opening that extends through the first end surface and a second opening that extends through the second end surface; and a scoop comprising opposite first and second side walls that each extend from the second end surface, the first side wall including a first top surface, the second side wall including a second top surface, the top surfaces extending parallel to one another along at least a portion of the scoop, the scoop comprising an arcuate inner surface that is continuous with the inner surface of the shaft and an opposite outer surface, the arcuate inner surface extending from the first top surface to the second top surface, the first and second side walls each being tapered from the second end surface to a distal end surface of the scoop, the scoop having a maximum width, the maximum width being equal to a maximum width of the shaft, the scoop including only one rib, the rib extending outwardly from the outer surface, the rib extending parallel to the longitudinal axis, the rib being positioned equidistant between the first and second side walls, the rib being spaced apart from the second top surface, a portion of the arcuate inner surface between the second end surface and the rib having a continuous radius of curvature from the first top surface to the second top surface.

* * * * *